(12) United States Patent
Karlsson et al.

(10) Patent No.: US 7,141,217 B2
(45) Date of Patent: *Nov. 28, 2006

(54) ELEVATED PRESSURE APPARATUS AND METHOD FOR GENERATING A PLURALITY OF ISOLATED EFFLUENTS

(75) Inventors: Arne Karlsson, Oslo (NO); Mark A. Krawczyk, Chicago, IL (US); Ara J. Alexanian, Des Plaines, IL (US); Duncan E. Akporiaye, Oslo (NO); Ivar M. Dahl, Oslo (NO)

(73) Assignee: UOP LLC, Des Plaines, IL (US)

( * ) Notice: Subject to any disclaimer, the term of this patent is extended or adjusted under 35 U.S.C. 154(b) by 580 days.

This patent is subject to a terminal disclaimer.

(21) Appl. No.: 10/313,334

(22) Filed: Dec. 5, 2002

(65) Prior Publication Data

US 2004/0109792 A1    Jun. 10, 2004

(51) Int. Cl.
B01J 9/00 (2006.01)

(52) U.S. Cl. ............ 422/130; 422/101; 422/102; 422/129; 436/37; 436/174; 436/180

(58) Field of Classification Search ............ 422/99, 422/102, 103, 129, 130, 131, 134, 101; 436/37, 436/174, 180

See application file for complete search history.

(56) References Cited

U.S. PATENT DOCUMENTS

| | | | | |
|---|---|---|---|---|
| 4,099,923 A * | 7/1978 | Milberger | ............ | 422/80 |
| 5,304,354 A | 4/1994 | Finley et al. | ............ | 422/196 |
| 5,489,726 A | 2/1996 | Huss, Jr. et al. | ............ | 585/671 |
| 5,609,826 A | 3/1997 | Cargill et al. | ............ | 422/99 |
| 5,612,002 A | 3/1997 | Cody et al. | ............ | 422/131 |
| 5,746,982 A | 5/1998 | Saneii et al. | ............ | 422/134 |
| 5,766,556 A | 6/1998 | DeWitt et al. | ............ | 422/131 |
| 5,785,927 A | 7/1998 | Scott et al. | ............ | 422/104 |
| 5,792,431 A | 8/1998 | Moore et al. | ............ | 422/134 |
| 6,149,882 A | 11/2000 | Guan et al. | ............ | 422/211 |
| 6,368,865 B1 | 4/2002 | Dahl et al. | ............ | 436/37 |
| 6,548,305 B1 * | 4/2003 | Deves et al. | ............ | 436/37 |
| 6,551,832 B1 | 4/2003 | Deves et al. | ............ | 436/37 |
| 6,737,026 B1 * | 5/2004 | Bergh et al. | ............ | 422/130 |
| 6,808,685 B1 * | 10/2004 | Akporiaye et al. | ............ | 422/130 |
| 2003/0040116 A1 | 2/2003 | Canos et al. | ............ | 436/37 |

FOREIGN PATENT DOCUMENTS

| | | |
|---|---|---|
| EP | 1 072 886 A1 | 5/2000 |
| WO | WO96/11878 A1 | 4/1996 |
| WO | WO97/30784 A1 | 8/1997 |
| WO | WO 97/32208 A1 | 9/1997 |

(Continued)

OTHER PUBLICATIONS

Akporiaye, D. E.; Dahl, I. M.; Karlsson, A.; Wendelbo, R. Angew Chem. Int. Ed. 1998, 37, 609-611.

(Continued)

*Primary Examiner*—Jill Warden
*Assistant Examiner*—Dwayne K. Handy
(74) *Attorney, Agent, or Firm*—John G. Tolomei; Maryann Maas

(57) ABSTRACT

An apparatus and a method for rapidly generating a plurality of isolated effluents have been developed. A specific embodiment involves screening a plurality of solids through simultaneously contacting the members of the plurality with a fluid, sampling the resulting fluids, and processing the resulting fluids to, for example, determine changes as compared to the feed fluid or as compared to other resulting fluids.

20 Claims, 2 Drawing Sheets

FOREIGN PATENT DOCUMENTS

| WO | WO 98/07026 A1 | 2/1998 |
| WO | WO 98/36826 | 8/1998 |
| WO | WO 99/19724 A1 | 4/1999 |
| WO | WO 99/34206 A1 | 7/1999 |
| WO | WO 01/59463 A1 | 8/2001 |

OTHER PUBLICATIONS

Senkam, S. M. Nature, Jul. 1998, 384(23), 350-353.

Bein, T. Angew. Chem. Int. Ed., 1999, 38, 323-326.

Holzwarth, A.; Schmidt, H.; Maier, W. F. Angew. Chem. Int. Ed., 1998, 37, 2644-2647.

Cong, P.; Doolen, R. D.; Fan, Q.; Giaquinta, D. M.; Guan, S.; McFarland, E. W.; Poojary, D. M.; Self, K.; Turner, H. W.; Weinberg, W. H. Angew Chem. Int. Ed. 1999, 38, 484-488.

Taylor, S. J.; Morken, J. P. Science, Apr. 1998, 280(10), 267-270.

Klien, J.; Lehmann, C. W.; Schmidt, H.; Maier, W. F. Angew Chem. Int. Ed. 1998, 37, 3369-3372.

* cited by examiner

US 7,141,217 B2

ELEVATED PRESSURE APPARATUS AND METHOD FOR GENERATING A PLURALITY OF ISOLATED EFFLUENTS

FIELD OF THE INVENTION

The present invention relates to an apparatus and a method for rapidly generating a plurality of isolated effluents. A specific embodiment involves screening a plurality of solids at elevated pressure through simultaneously contacting the members of the plurality with a fluid, sampling the resulting effluents, and processing the resulting effluents to, for example, determine changes as compared to the feed fluid or as compared to other resulting effluents.

BACKGROUND OF THE INVENTION

Developments in combinatorial chemistry have concentrated on the synthesis of chemical compounds. For example, U.S. Pat. Nos. 5,612,002 B1 and 5,766,556 B1 disclose a method and apparatus for multiple simultaneous synthesis of compounds. WO 97/30784-A1 discloses a microreactor for the synthesis of chemical compounds. Akporiaye, D. E.; Dahl, I. M.; Karlsson, A.; Wendelbo, R. Angew Chem. Int. Ed. 1998, 37, 609–611 disclose a combinatorial approach to the hydrothermal synthesis of zeolites, see also WO 98/36826. Other examples include U.S. Pat. Nos. 5,609,826 B1, 5,792,431 B1, 5,746,982 B1, and 5,785,927 B1, and WO 96/11878-A1.

More recently, combinatorial chemistry approaches have been applied to catalyst testing in an attempt to expedite the testing process. With the growing number of materials being synthesized combinatorially, more efficient methods of evaluating the materials are needed. Especially needed are combinatorial methods for the evaluation of solids that are designed to keep pace with the speed of combinatorial synthesis. For example, WO 97/32208-A1 teaches placing different catalysts in a multicell holder. The reaction occurring in each cell of the holder is measured to determine the activity of the catalysts by observing the heat liberated or absorbed by the respective formulation during the course of the reaction, and/or analyzing the products or reactants. Thermal imaging had been used as part of other combinatorial chemistry approaches to catalyst testing; see Holzwarth, A.; Schmidt, H.; Maier, W. F. Angew. Chem. Int. Ed., 1998, 37, 2644–2647, and Bein, T. Angew. Chem. Int. Ed., 1999, 38, 323–326. Thermal imaging may be a tool to gain knowledge of some semi-quantitative information regarding the activity of the catalyst, but it provides no indication as to the selectivity of the catalyst.

Some attempts to acquire information as to the reaction products in rapid-throughput catalyst testing are described in Senkam, S. M. Nature, July 1998, 384(23), 350–353, where laser-induced resonance-enhanced multiphoton ionization is used to analyze a gas flow from each of the fixed catalyst sites. Similarly, Cong, P.; Doolen, R. D.; Fan, Q.; Giaquinta, D. M.; Guan, S.; McFarland, E. W.; Poojary, D. M.; Self, K.; Turner, H. W.; Weinberg, W. H. Angew Chem. Int. Ed. 1999, 38, 484–488 teaches using a probe with concentric tubing for gas delivery/removal and sampling. Only the fixed bed of catalyst being tested is exposed to the reactant stream, with the excess reactants being removed via vacuum. The single fixed bed of catalyst being tested is heated and the gas mixture directly above the catalyst is sampled and sent to a mass spectrometer.

Combinatorial chemistry has been applied to evaluate the activity of catalysts. Some applications have focused on determining the relative activity of catalysts in a library; see Klien, J.; Lehmann, C. W.; Schmidt, H.; Maier, W. F. Angew Chem. Int. Ed. 1998, 37, 3369–3372; Taylor, S. J.; Morken, J. P. Science, April 1998, 280(10), 267–270; and WO 99/34206-A1. Some applications have broadened the information sought to include the selectivity of catalysts. WO 99/19724-A1 discloses screening for activities and selectivities of catalyst libraries having addressable test sites by contacting potential catalysts at the test sites with reactant streams forming product plumes. The product plumes are screened by passing a radiation beam of an energy level to promote photoions and photoelectrons, which are detected by microelectrode collection. WO 98/07026-A1 discloses miniaturized reactors where the effluent is analyzed during the reaction time using spectroscopic analysis.

Some commercial processes have operated using multiple parallel reactors where the products of all of the reactors are combined into a single product stream; see U.S. Pat. Nos. 5,304,354 B1 and 5,489,726 B1. Another patent, U.S. Pat. No. 6,149,882 B1 teaches an apparatus having a plurality of vessels and valves and conduits for sequentially sampling the effluent of the vessels or a sample probe positioned next to the effluent to transport sampled fluid to a detector.

Applicants have developed a combinatorial method and apparatus particularly suited for the generation of a plurality of independent effluents. The effluents are generated in parallel and are kept isolated from one another. The effluents may be further processed by, for example, analyzing the composition of the effluents, by further reacting the effluents, by further treating the effluents, and the like. Multiple solids are contacted with a feed fluid in parallel with the resulting effluents being sampled and then analyzed for changes as compared to the feed fluid. The apparatus and method is particularly beneficial when generating the plurality of effluents at elevated pressures. Furthermore, the apparatus is adaptable for generating the effluents from the combination of gas feed and liquid feeds. A diluent gas may also be introduced to the vessels. The parallel reactions and the analyses provide a means for the high throughput evaluation of multiple solids or mixtures of solids.

SUMMARY OF THE INVENTION

One purpose of the present invention is to provide an apparatus for generating a plurality of effluents where the apparatus consists of a multiplicity of vessels containing solids with each vessel having an inlet and an outlet, a multiplicity of effluent conduits in fluid communication with the outlets of the vessels each effluent conduit which divides into a sampling conduit and a vent conduit, each sampling conduit containing a restrictor, at least one sampling valve in fluid communication with the sampling conduits, a bypass conduit and a processing conduit in fluid communication with the sampling valve, and a processing device in fluid communication with the processing conduit from the sampling valve. The invention is particularly useful to evaluate a plurality of solids at elevated pressures.

Another purpose of the present invention is to provide a method of generating a plurality of effluents where a plurality of solids are contained in a set of vessels with each vessel having an inlet and an outlet. The solids are contacted, simultaneously, at elevated pressure, with a feed fluid to generate vessel effluents. Each effluent is split into a sample portion and a vent portion. The pressure of the sample portions is reduced and the sample portions are routed to a sampling valve. A sample portion is selected using the sampling valve and the selected sample portion is processed.

The further processing may be analyzing the vessel effluents to determine changes in the vessel effluents as compared to the feed fluid or as compared to other vessel effluents. Such analyses may be particularly useful in evaluating a plurality of solids.

DETAILED DESCRIPTION OF THE INVENTION

Figure 1:
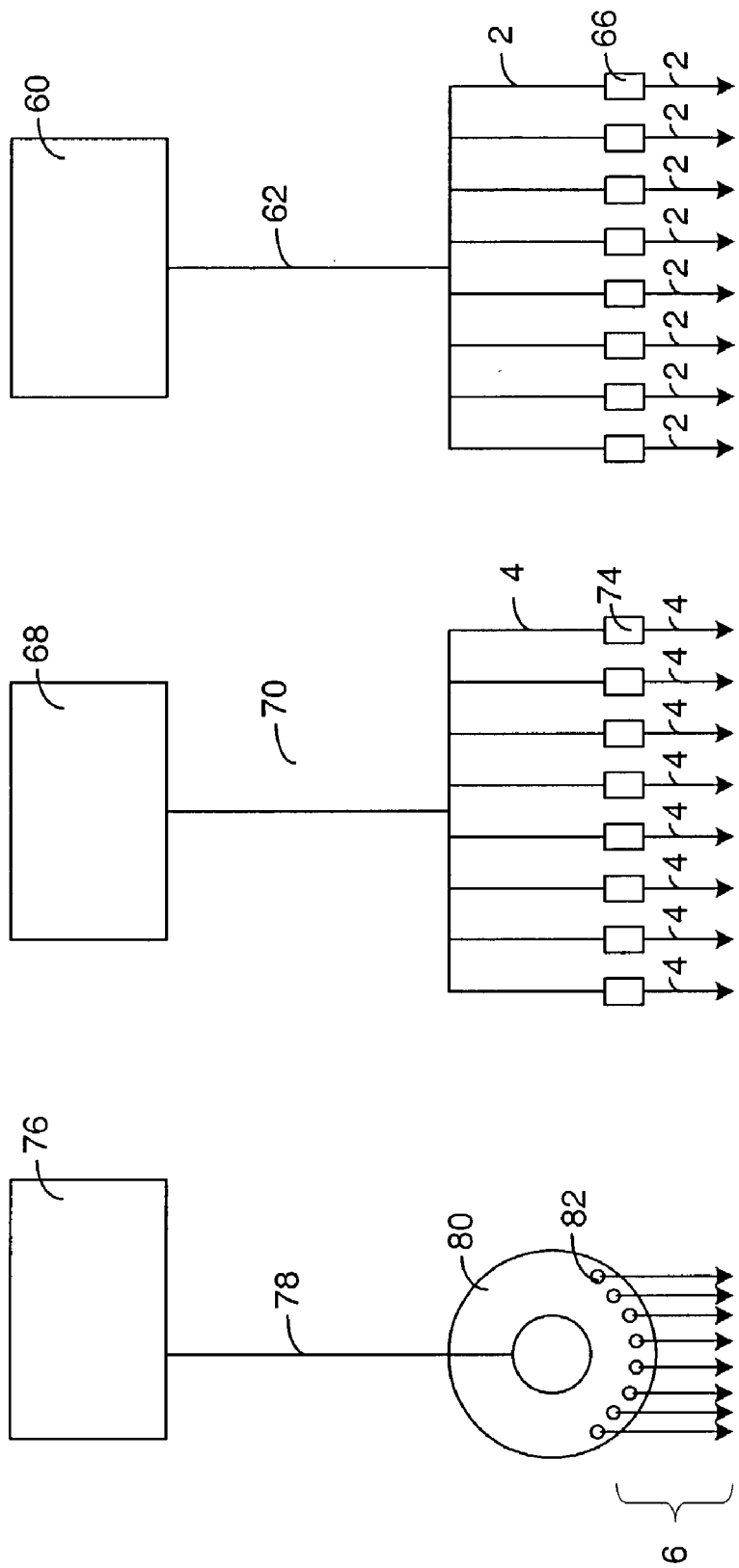
FIG. 1 is a schematic drawing of the feed system of the embodiment of the invention shown in FIG. 2.

An apparatus and a method are provided for combinatorial generation of a plurality of effluents. In general terms, a feed fluid is contacted simultaneously with a plurality of solids where each of the solids is housed in an individual vessel in order to generate vessel effluents. The feed fluid may be a gas or a gas and a liquid, and the vessel effluents may be mixed with a diluent gas. The contacting may be conducted at elevated temperature and elevated pressure. Each vessel effluent is separated into a sample portion and a vent portion. The vent portions may be combined and directed to waste. The pressure of the sample portions are reduced and directed to a sampling valve. Using the sampling valve, a single sample portion is selected for further processing. For example, when screening a plurality of solids, the sample portion selected is introduced into, for instance, one or more gas chromatographs for analysis. Changes in the effluents as compared to the feed or to each other are used to determine properties of the plurality of solids being tested. The results of the analysis may also indicate those solids whose performance warrants further investigation. Sample portions that are not selected are combined into a bypass line which bypasses the processing device. The bypass line is connected to the combined vent portions line.

The plurality of effluents generated by the subject invention are further processed by, for example without limitation, further reacting the effluents, separating the effluents, treating the effluents with an adsorbent, analyzing the effluent, and the like. Any relevant processing device may be used in the processing; reactors, adsorbers, analytical instrumentation, etc. The discussion herein will focus on analyzing the plurality of effluents as is useful in screening a plurality of solids.

The apparatus and method of the present invention may be used to screen the plurality of samples for any property that can be determined through measuring or monitoring the changes between the feed fluid and the effluent or between the multiple effluents. For example, catalytic activity of a solid may be evaluated by analyzing the concentration of the reactants in the feed fluid as compared to the reactants and products of each reactor effluent. With the present invention, those solids showing the greatest conversion to the products or perhaps the greatest selectivity to the desired product could be determined expediently. Similarly, adsorptivity of solids may be evaluated by comparing the concentration of an adsorbate in a feed stream with the concentration of the same adsorbate in each of the reactor effluents. Those solids having the greatest reduction in adsorbate from the feed concentration to the effluent concentration may be quickly identified for further testing and investigation. It is also contemplated that a property of interest may be determined by comparing the effluents to each other as opposed to, or in addition to, the feed fluid. An important benefit of the present invention is that such identifications can be produced rapidly for a large number of samples. In the same amount of time historically required to evaluate a single solid, with the present invention a multiplicity of solids can be evaluated.

The present invention is particularly beneficial in applications where the fluid(s) are contacted with the solids at operating conditions that include elevated pressures. For example, pressures ranging from about 345 kpag (50 psig) to about 3447 kPa (500 psig) are typical for some applications. Additionally, the present invention is beneficial where both a liquid feed and a gas feed are introduced to the vessels containing the plurality solids. Finally, the present invention is especially beneficial in applications where a diluent gas is to be mixed with the effluents of the vessel. In a specific embodiment, the diluent gas is mixed with effluents of a treatment zone within the vessel before the effluents exit the vessel.

Figure 2:
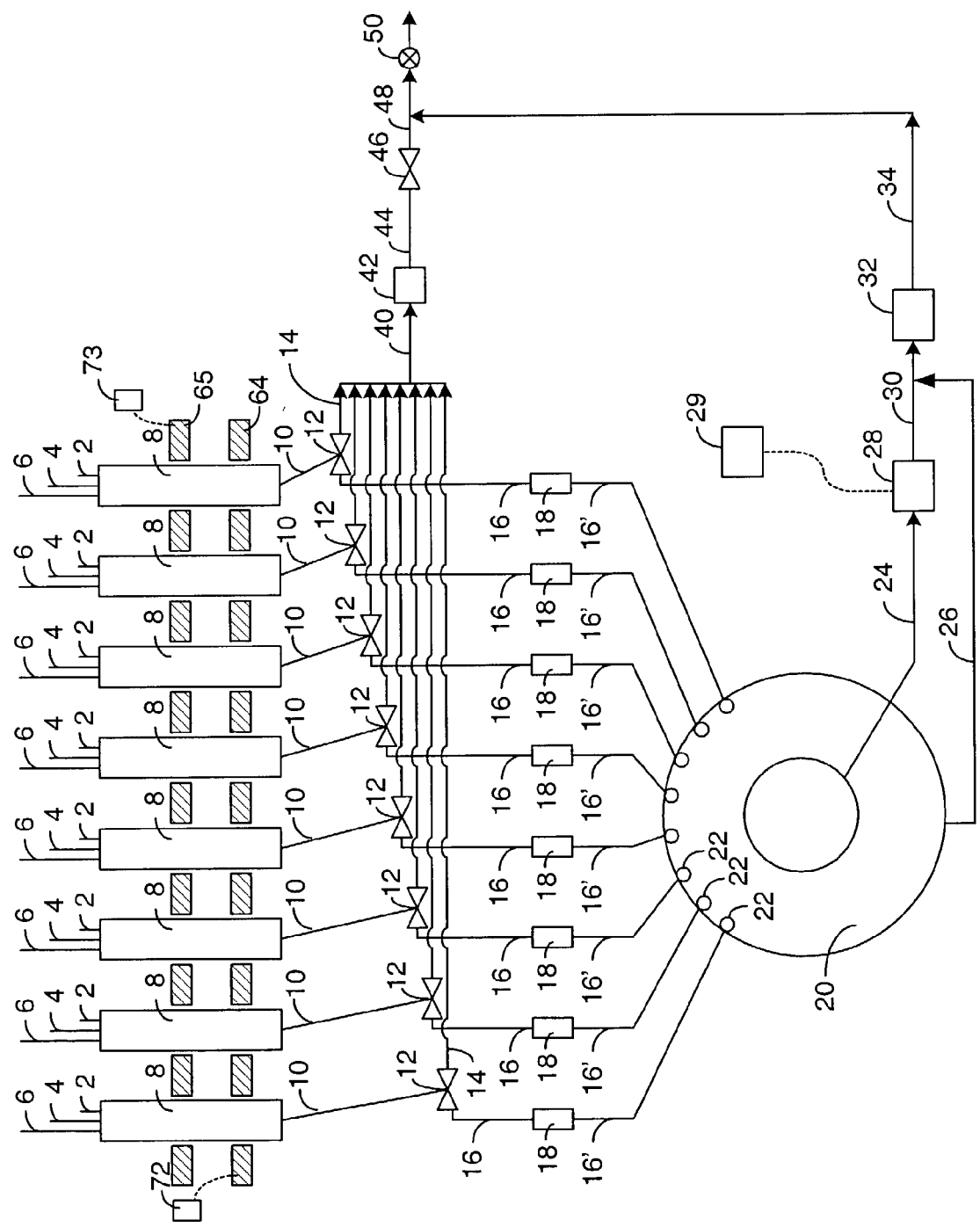
FIG. 2 is a schematic drawing of a portion of one embodiment of the invention, an apparatus for rapidly screening solids. The figure shows only the first of multiple banks of reactors.

For ease of explanation, the process and apparatus will be described herein as a 48-reactor system where the reactors are grouped into six banks containing eight reactors in each bank. FIG. 1. shows the source fluids and the source fluid distribution. FIG. 2 shows only a portion of the source fluid distribution and only the first bank of eight reactors and associated equipment. The other five banks of eight reactors each, and the equipment associated with each bank of reactors, are not shown. Although the vessels are referred to throughout as "reactors" it must be emphasized that vessels other than reactors are suitable for the present invention. "Reactors" are merely used in reference to a specific embodiment of the invention.

Turning to FIG. 1, the process begins with one or more source fluids in containers 60 and 68. At least one source fluid is preferably gaseous, and the other may be liquid or gas. In this example, the source fluid from container 60 is a gas and the source fluid from container 68 is a liquid. The gas fluid may be saturated with other components. For purposes of this description, the gas is contained within container 60 which is a cylinder. The pressure of the source gas is maintained above the reaction pressure and may be stepped down through, for example, a series of reducing valves. The liquid may be from a pressurized reservoir tank and may be a mixture of two or more liquids. The liquid may be maintained at reaction pressure using inert gas such as helium, nitrogen or argon, or the liquid could be maintained at a pressure lower than reaction pressure and pumped to a higher pressure when necessary.

A main gas conduit 62 directs gas from cylinder 60 to be split into eight individual gas feed lines 2. Note that in alternative embodiments, main gas conduit 62 can be connected to a selector that operates to select gas from two or more reservoirs. It is preferred that the stream in the main gas conduit 62 be allowed to separate into the eight individual gas feed lines 2 by passing through, for example, branch connectors. The purpose of the branch connectors is merely to split the source fluid stream into eight portions. It is not necessary that the eight separated portions be regulated as to mass flow at this point. After the separation via branch connectors, each individual gas feed line is equipped with a mass flow controller 66. The mass flow controllers are used to control the flow of the gas feed to the reactor vessels. Similarly, a main liquid conduit 70 directs liquid from reservoir 68 to be split into eight individual liquid feed lines 4. Again, the purpose of the branch connectors is merely to split the source liquid stream into eight portions, and not to regulate mass flow at this point. After the separation via branch connectors, each individual liquid feed line is equipped with a mass flow controller 74. The mass flow controllers are used to control the flow of the liquid feed to the reactor vessels. Because each of the feed lines 2 is equipped with an individual mass flow controller, the split of the gas of line 62 into lines 2 and the split of the liquid of line 70 into lines 4 is not controlled. Pressure transducers may be used to monitor the pressure of any of the fluid in lines 62, 2, 70 and 4.

FIG. 1 further shows the optional diluent gas source 76. The diluent gas is mixed with the effluents to prevent components in the effluent from condensing in the conduits and fouling the effluent lines. The diluent gas may also be used to maintain sufficient pressure in the reactor and streams. As with the gas fluid discussed above, the pressure of the diluent gas at the source is preferably above the reaction pressure. The diluent gas is conducted from source 76 through conduit 78 and to valve 80. Valve 80 splits the diluent gas into eight portions that are conducted in lines 6. Other devices such as a manifold with restriction orifices or individual restrictors may also be successfully employed in the present invention. Alternatively, each individual diluent gas line may be equipped with a mass flow controller. Restrictor-type splitting of the diluent gas is less costly than individual mass flow controllers, and the need to vary the diluent gas flow between the different reactors is lower thereby rendering the restrictor-type splitting of the gas fluid to be the preferred embodiment. Capillary-type or capillary tube restrictors are suitable devices for distributing the diluent fluid into portions.

It is preferred that the diluent gas be mixed with gas resulting from the feed contacting the solids at a point after contacting the solids and before the effluent exits the vessel. It is possible to have the diluent gas follow the same flow path as the feed, but then the treatment zone of the vessel may need to be enlarged to accommodate additional fluid flow. Also, using the same flow path may change the reaction characteristics such as conversion, selectivity, and yield since with the addition of the diluent, the reactant concentrations were altered. With the diluent gas routed around the treatment zone of the vessel but yet mixing with the resulting effluent at a location near to the treatment zone and preferably within the vessel, the dilution function is accomplished without enlarging the treatment zone. In addition, the location is most likely at a temperature near to the treatment temperature thereby eliminating the need for heat traced lines to conduct the effluent to a location for mixing with the diluent.

Since each gas feed line 2 and each liquid feed line 4 to each of the reactor vessels has its own individual mass flow controller, the system is very versatile. For example, each of the gas feed lines 2 may be independently controlled via the mass flow controllers 66 to allow the same space velocity of the gas to pass through each of the gas feed lines, or the mass flow controllers 66 may be independently controlled so that a different space velocity of the gas feed passes through one or more of the gas feed lines 2. At the same time, each of the liquid feed lines 4 may be independently controlled via the mass flow controllers 74 to allow the same space velocity of the liquid to pass through each of the liquid feed lines, or the mass flow controllers 74 may be independently controlled so that a difference space velocity of the liquid feed passes through one or more of the liquid feed lines 4. The particular application and the data desired or variables being investigated are factors to be considered when determining the flow rates of the fluids to the reactor vessels.

FIG. 1 shows a single gas feed source, 60, and a single liquid source, 68, but in other embodiments additional sources may be employed. A set of six selector valves (not shown) are connected via branch connectors to each of the fluid source lines; i.e., each valve in the set of six is connected via branch connectors to each of the fluid source lines. In the present example, six selector valves are required because there are six banks of reactors. In other applications, the number of selector valves may vary. The purpose of the selector valve is to allow for the selection of the source fluid that will be conducted to the reactors. In this example, the selector valves for the gases are preferably 8-port valves, although various other devices may be used. The valves are positioned so that the selected source fluids are able to pass through the valves while the source fluids that are not selected are blocked and unable to pass through the valves. The selection valve and corresponding source fluids allow the solids to be pretreated using a variety of gasses, oxidative, reductive, or neutral, as well as providing the co-feed containing reactants.

From the mass flow controllers 66 and 74, the gas feed stream in lines 2 and the liquid feed stream in lines 4 are simultaneously introduced to the individual reactor vessels 8. The reactors, 8, may be of any type used in combinatorial evaluations, with preferred reactors being of the type described in U.S. application Ser. Nos. 10/095,879, 10/095,934, and 10/095,395. Other suitable reactors include EP 1108467 A2, U.S. Pat. Nos. 6,342,185 and 6,327,344. The number of vessels, e.g., reactors in this embodiment, making up the multiplicity may vary from two vessels to hundreds of vessels. It is preferred to have at least eight or at least sixteen vessels in the multiplicity and it is most preferred to have forty-eight vessels in the multiplicity. Diluent gas in lines 6 may also be simultaneously introduced to vessels 8. However, it is preferred that diluent gas be routed around the reaction zone of the vessels 8 and mix with the effluent of the reaction zone before exiting the vessel. A preferred reactor that allows for the diluent gas to bypass the reaction zone is found in U.S. application Ser. Nos. 10/095,879, 10/095,934, and 10/095,395. Such a configuration prevents unnecessarily large volumes from flowing through the reaction zones, while at the same time providing a mechanism to prevent components in the effluent of the reaction zone from condensing in the lines. Fouling or plugging of the effluent lines can result in a failure of the system to operate properly and possibly false results.

The vessels house solids that may interact with the feed streams. For example, the reactors may house catalysts that catalyze a chemical reaction and yield products, or the reactors may house adsorbents that adsorb one or more components from the source fluid. It is within the scope of the invention that the reactor may house a mixture of catalyst and adsorbent. The solids of interest may be present as solid particles or may be supported by solids. Each of the reactors may contain different solids, different mixtures of solids, the same compositional mixture of solids where the components are in different ratios, or the like. Replicates may be included within the array of solids. Although not necessary, typically, the solids will be present in a fixed bed. The reactor feed streams will flow through the interstices of the fixed bed providing contact between the solid and the reactor feed stream. The reactors may be associated with at least heater, 64, having a controller, 72, to provide controlled heat to the reaction zone of the reactors. Similarly, the reactors may be associated with heater 65 having controller 73 to provide controlled heater to another zone of the reactors such as an evaporation zone. Alternatively, individual heaters may be employed with each heater associated with a specific vessel.

The effluent from each of the reactors is conducted simultaneously, yet separately, in lines 10 to gas splitting devices 12. Gas splitting devices 12 can be, for example, SGE valves or branch connectors. FIG. 2 shows gas splitting devices 12 as two-way valves which direct flow into two conduits in one position and blocks flow in the other position. In this particular example, as the effluent passes through gas splitting devices 12, the bulk of each effluent stream is directed into vent lines 14 and a smaller portion of each effluent in directed into samples lines 16. The amount of effluent directed into sample lines 16 and vent lines 14 depends upon the specific application. However, factors such as the amount of effluent necessary for further processing are considered. For example, if the further processing is compositional analysis using gas chromatography, enough effluent should be directed to the sample lines 16 so that proper technique may be used in the gas chromatographic analysis. The plurality of vent lines 14 can be combined into a single vent line 40 which is equipped with vapor-liquid disengaging volume 42 and back pressure regulator 46. For ease of understanding, the vapor-liquid disengaging volume 42 will be referred to as a preferred embodiment of knock-out pot or condenser 42. As effluent passes from line 40 and through knock-out pot 42, liquid is separated from gaseous material. Knock-out pots are known in the industry and will not be described in detail herein. The preferred knock-out pot temperature is below ambient. This design allows for pressure regulation of the gaseous content of the effluent. The gaseous material from knock-out pot 42 after passing through back-pressure regulator 46 may be combined with line 24 and the combined stream passed to moisture analyzer 50.

Sample lines 16 are equipped with pressure reducing devices such as restrictors 18 that operate to reduce the pressure in the lines and to restrict the amount of fluid passing through to an appropriate amount. The pressure in lines 16 between gas splitting devices 12 and restrictors 18 is near to the, reaction pressure. After passing through the restrictors 18, the effluent in lines 16', between restrictors 18 and sampling valve 20, is at a reduced pressure as compared to the pressure in lines 16 and preferably close to atmospheric pressure. The pressure may still be elevated slightly above atmospheric to ensure the flow continues through the system according to the general principal that fluid flow is generated from an area of high pressure to an area of lower pressure. The present system is particularly advantageous when the further processing of the effluents require a pressure less than the pressure used in the reaction vessels 8. For example, when the further processing is analytical analysis such as near-IR, FTIR, etc., which is conducted at a pressure less than the reaction pressure, the present system is readily adaptable to provide the stream to be analyzed at a pressure suitable to the analytical method.

Reduced-pressure sampling lines 16' carry the effluents to a sampling valve 20. Each of the sampling lines 16' is connected to an individual port of sampling valve 20. Sampling valve 20 allows for the effluent in one of the sampling lines 16' to be selected for further processing with the rest of the effluents in sampling lines 16' bypassing the additional processing step. Sampling valve 20 may be cycled through all of its positions so that the effluent in each sampling line 16' is selected in sequence for additional processing. How the cycling is timed is dependent upon the particular application and may be quite dependent upon the nature of the additional processing. For example, when the additional processing is analysis of the effluent using gas chromatography, the cycle time of the valve may be dependent upon the time needed to complete the chromatographic analysis. It is within the scope of the present invention to utilize sampling valves that simultaneously select two or more effluents for parallel additional processing when multiple processing devices are available. It is preferable that each selected effluent remain isolated from other effluents until the additional processing is completed. The exact type of valves used for sampling valve 20 will vary with the application, suitable examples include Valco high temperature and high pressure valves. The valves may be any type of device or valve that allows for a selection of at least one fluid from a multiple of fluid flows with the selected fluid flow directed to a first conduit and the remainder of the fluid flows combined and directed to a second conduit.

The selected effluent is directed from sampling valve 20 in line 24 to a processing device 28. An interface may be used to allow for a plurality of processing devices. The processing device may be any device used to treat or measure the effluent such as analytic systems or detectors. For ease of explanation, a gas chromatograph will be the analytical detection device described herein. However, other analytical techniques such as liquid chromatography, infrared spectroscopy, uv-vis spectroscopy, ultraviolet spectroscopy, visible spectroscopy, fluorescence spectroscopy, infrared thermography, nuclear magnetic resonance, paramagnetic resonance, X-ray adsorption, X-ray photoelectron spectroscopy, Raman spectroscopy and combinations thereof may be similarly employed. Other detectors include ion selective electrodes, potentiometric devices, and photo oxidation analyzers. Other processing devices besides a detector may be used to process the isolated effluents. A reactor may be used to further react the effluents, a separator may be used to separate the effluents, or a treatment vessel containing, for example, an adsorbent may be used to treat the effluents. The processing device may be controlled by a microprocessor 29 which may also store any data generated by the processing device. The effluent from the processing device 30 is passed to knock-out pot 32 to remove liquid and the resulting gas is flowed through line 34 and preferably added to the combined vent effluent in line 48. In other embodiments, the resulting gas flowed through line 34 may be, for example, vented independently of combined vent effluent in line 48.

In this example, the reactor vessel effluents in lines 16' that are not selected for further processing are combined by sampling valve 20 into line 26. The effluents in line 26 are combined with line 30 and introduced to knock-out pot 32 to condense liquid, and the resulting gas stream is flowed through line 34 and added to the combined vent effluents in line 48. Again, alternative embodiments do not require the resulting gas stream flowed through line 34 to be added to the combined vent effluents in line 48. Depending upon the to compounds present in the system, vent effluent may be treated to remove, convert, or neutralize specific components before being vented. Periodically, the knock-out pots 42 and 32 may be emptied of collected liquid.

A trace of the path of a single set of feeds through the system of FIG. 2 is as follows. Gas feed in line 2, liquid feed in line 4, and diluent gas in line 6 are introduced at elevated pressure to reactor 8. Reactor 8 contains catalyst and has an evaporation stage to evaporate the liquid feed and mix with the gas feed so that the combined feeds in a gaseous state are contacted with a catalyst to generate an effluent. The evaporation stage of reactor 8 is heated by heater 65 and reaction stage of reactor 8 is heated by heater 64. After contacting the catalyst, the reaction stage effluent is diluted with diluent gas in reactor 8. The reactor effluent is conducted in line 10 to gas splitter 12 where a portion of the effluent is directed to line 14 to be vented, and a smaller portion of the effluent is directed to line 16 for further processing. Line 16 is equipped with restrictor 18 to reduce the pressure of the reactor effluent. The reactor effluent of line 16', now at a reduced pressure, is introduced to a port of sampling valve 20. If the cycle position of sampling valve 20 is such that the port of interest is selected, the reactor effluent is directed through line 24 and into a processing device 28. As an example, processing device 28 may be a gas chromatograph. In this embodiment, after processing, the processing device effluent is conducted in line 30 to a knock-out pot 32 for removal or condensation of liquid. The resulting gas stream from knock-out pot 32 is flowed through line 34 and added to the vent effluents in line 48. If, on the other hand, the cycle of sampling valve 20 is such that the port of interest is not selected, the reactor effluent is combined with other non-selected effluents and the combined effluents are directed through line 26 adding with line 30 downstream of processing device to knock-out pot 32 for removal or condensation of liquid. The resulting gas stream from knock out pot 32 is flowed through line 34 and added to the vent effluents in line 48.

The portions of the reactor effluents in lines 14 are combined into a single vent effluent 40 which is passed to knock-out pot 42 for the removal of liquid. The resulting gas stream in line 44 is reduced in pressure by back-pressure regulator 46 to form a reduced-pressure combined vent effluent stream 48. The back-pressure regulator 46 in combination with the restrictors 18 and the sources 60, 68 and 76 operate to control the pressure within the reactors and the flow of fluid through the system. Typical pressures the system may be expected to operate within range from about 345 kPag (50 psig) to about 3447 kPag (500 psig) and different restrictors and back-pressure regulators may be selected depending upon the particular pressure selected.

What is claimed is:

1. An apparatus for generating a plurality of effluents comprising:
   a) a multiplicity of vessels containing solids, each vessel having an inlet and an outlet;
   b) a multiplicity of effluent conduits, a multiplicity of sampling conduits, and a multiplicity of venting conduits wherein each effluent conduit is in fluid communication with a corresponding outlet of the vessel, a corresponding sampling conduit and a corresponding vent conduit; each sampling conduit containing a pressure reducing device;
   c) at least one sampling valve in fluid communication with the multiplicity of sampling conduits;
   d) a bypass conduit and a processing conduit in fluid communication with the sampling valve; and
   e) a processing device in fluid communication with the processing conduit from the sampling valve.

2. The apparatus of claim 1 wherein the bypass conduit further comprises a vapor-liquid disengaging volume.

3. The apparatus of claim 1 wherein the pressure reducing device is a restrictor.

4. The apparatus of claim 1 further comprising a combined vent conduit in fluid communication with at least two of the vent conduits, said combined vent conduit further comprising a vapor-liquid disengaging volume and a pressure regulator.

5. The apparatus of claim 1 further comprising a processing device effluent in fluid communication with the processing device, and a combined vent conduit vent in fluid communication with at least two of the vent conduits, the processing device effluent and the bypass conduit.

6. The apparatus of claim 1 wherein the processing device is selected from the group consisting of a detector, a reactor, and a treatment vessel.

7. The apparatus of claim 1 wherein said vessels are grouped into banks of vessels wherein each bank of vessels is associated with an independent set of elements (b) through (e) of claim 1.

8. The apparatus of claim 6 wherein the detector is selected from the group consisting of a gas chromatograph, an infrared detector, a uv-vis detector, an ultraviolet detector, a visible detector, fluorescence detector, an infrared thermography detector, a nuclear magnetic resonance detector, a paramagnetic resonance detector, a X-ray adsorption detector, a X-ray photoelectron detector, a Raman detector and combinations thereof.

9. The apparatus of claim 1 further comprising a set of feed conduits, the feed conduits in fluid communication with an associated vessel and a feed selector valve, the feed selector valve in fluid communication with two or more feed sources.

10. The apparatus of claim 1 further comprising a multiplicity of gas feed conduits in fluid communication with the multiplicity of vessels.

11. The apparatus of claim 10 further comprising a multiplicity of liquid feed conduits in fluid communication with the multiplicity of vessels.

12. The apparatus of claim 11 further comprising a multiplicity of diluent conduits in fluid communication with the multiplicity of vessels.

13. The apparatus of claim 10 wherein each gas feed conduit further comprises a mass flow controller.

14. The apparatus of claim 11 wherein each liquid feed conduit further comprises a mass flow controller.

15. The apparatus of claim 12 further comprising a diluent source conduit in fluid communication with at least one pressure reducing device, the pressure reducing device in fluid communication with at least one of the diluent conduits.

16. The apparatus of claim 1 wherein the vessels are comprised of a housing, a sleeve and an insert.

17. The apparatus of claim 16 wherein the vessels further comprise an evaporation zone and a reaction zone.

18. The apparatus of claim 1 further comprising at least one heater located proximate to the vessels.

19. The apparatus of claim 1 further comprising a temperature control system for regulating the temperature of the vessels.

20. The apparatus of claim 1 further comprising a gas splitting device in fluid communications with the pair of sampling conduit and vent conduit and the corresponding effluent conduit.

* * * * *